United States Patent
Arnold et al.

(10) Patent No.: US 7,242,017 B2
(45) Date of Patent: Jul. 10, 2007

(54) DEVICE TO DETECT AND/OR CHARACTERIZE INDIVIDUAL MOVING OBJECTS HAVING VERY SMALL DIMENSIONS

(75) Inventors: Martin Arnold, Huefingen (DE); Norbert Irmer, Villingen-Schwenningen (DE)

(73) Assignee: Minebea Co., Ltd., Nagano-ken (JP)

( * ) Notice: Subject to any disclaimer, the term of this patent is extended or adjusted under 35 U.S.C. 154(b) by 7 days.

(21) Appl. No.: 11/029,924

(22) Filed: Jan. 5, 2005

(65) Prior Publication Data

US 2005/0151097 A1    Jul. 14, 2005

(30) Foreign Application Priority Data

Jan. 7, 2004    (DE)    ........................ 10 2004 001 157

(51) Int. Cl.
*G01N 15/06*    (2006.01)

(52) U.S. Cl. ........................ 250/574; 356/336; 356/338

(58) Field of Classification Search ........ 250/573–576, 250/227.11, 227.25, 227.28, 227.29, 227.3; 356/335–343
See application file for complete search history.

(56) References Cited

U.S. PATENT DOCUMENTS

| | | | | |
|---|---|---|---|---|
| 4,157,468 A | * | 6/1979 | Primiano | ...................... 377/10 |
| 4,427,143 A | | 1/1984 | Hyatt | .......................... 250/574 |
| 5,352,901 A | * | 10/1994 | Poorman | .................... 250/574 |
| 5,562,214 A | * | 10/1996 | Castaneda et al. | .......... 209/564 |
| 6,075,239 A | | 6/2000 | Aksyuk et al. | ............. 250/229 |
| 6,118,531 A | * | 9/2000 | Hertel et al. | ................ 356/336 |
| 6,593,573 B1 | * | 7/2003 | McCann et al. | ........ 250/339.12 |
| 6,803,594 B2 | * | 10/2004 | Spolaczyk et al. | ........... 250/574 |
| 2002/0047633 A1 | | 4/2002 | Jurs et al. | .................... 315/291 |
| 2003/0071197 A1 | | 4/2003 | Sugiyama | ............... 250/214 A |

FOREIGN PATENT DOCUMENTS

| | | |
|---|---|---|
| DE | 201 04 248 U1 | 6/2001 |
| DE | 100 33 077 A1 | 7/2002 |
| DE | 43 34 785 C2 | 4/2003 |
| DE | 203 042 11 U1 | 7/2003 |
| WO | WO 81/01200 | 4/1981 |

OTHER PUBLICATIONS

U.S. Appl. No. 10/918,890, Martin et al, Device to Detect Individual Moving Objects Having Very Small Dimensions, filed Aug. 16, 2004.

* cited by examiner

*Primary Examiner*—Thanh X. Luu
(74) *Attorney, Agent, or Firm*—Baker & Daniels LLP

(57) ABSTRACT

The invention relates to a device to detect and/or characterize individual moving objects having very small dimensions which comprises a photo electric sensor having at least one light beam emitter and one light beam receiver in which the objects that are to be measured move through the optical path of the photo electric sensor, a first number of optical waveguides whose inputs are connected to the light beam emitter, the light beams emitted by the outputs of the optical waveguides forming the optical path of the photo electric sensor, a second number of optical waveguides whose inputs pick up the light beams emitted by the optical waveguides and whose outputs are connected to the light beam receiver, the outputs of the optical waveguides and the inputs of the optical waveguides being arranged in the form of a ring on a common plane, and an evaluation unit which is coupled to the light beam receiver and records the change in light intensity of the photo electric sensor produced by the objects passing through the optic path.

16 Claims, 3 Drawing Sheets

DEVICE TO DETECT AND/OR CHARACTERIZE INDIVIDUAL MOVING OBJECTS HAVING VERY SMALL DIMENSIONS

BACKGROUND OF THE INVENTION

The invention relates to a device to detect and/or characterize individual moving objects having very small dimensions, particularly dimensions in the sub-mm range.

OUTLINE OF THE PRIOR ART

Photo electric sensors are frequently used to detect moving objects. Photo electric sensors not equipped with additional beam-forming optics that are available on the market have measurement volumes which are too large, i.e. the diameter of the optical path is too large to detect very small individual objects with a high repeat rate and with short object spacing. Beam-forming optics that could remedy this problem need a large installation space compared to the very small objects. If there is only a restricted installation space available, these kinds of photo electric sensors cannot be employed.

Existing evaluation electronics analyze the changes in the signal when an object passes by and thus recognizes the objects. Particularly in the case of very small objects, however, environmental influences, electrical disturbances and transit phenomena result in faulty detection since the signal picked up by the light beam receiver is very small compared to the interfering signals. These kinds of evaluation circuits do not produce a counting result that is sufficiently reliable in order to count, for example, drops of liquid that have a diameter of 200 μm or less.

From the unpublished patent application DE 103 38 108.2, a photo electric sensor having at least one light beam emitter and one light beam receiver is known in which the objects that are to be measured move through the optical path of the photo electric sensor. The photo electric sensor comprises a first bundle of optical waveguides (OWG), whose inputs are connected to the light beam emitter and whose outputs are arranged in a row alongside each other, the light beams emitted by the outputs forming the optical path of the photo electric sensor. A second bundle of optical waveguides are provided which are arranged in a row alongside each other whose inputs pick up the light beams emitted by the first bundle of optical waveguides and whose outputs are connected to the light beam receiver. Moreover, an evaluation unit is also provided which is coupled to the light beam emitter and the light beam receiver and which registers a change in the received light intensity of the photo electric sensor produced by the objects passing through the optical path.

In this line-like arrangement of similar kinds of optical waveguides, the area of shadow $A_{ObjectShadow}$ of an object that is to be detected only covers a small part of the optical path, i.e. the total area of all optical waveguides. The total area $A_{Tot\_OWG}$ corresponds to the number of receiver-optical waveguides multiplied by the area $A_{OWG}$ of each waveguide. The change in signal at the receiver is thus proportional to the quotient of the area of shadow cast by the object and the total area:

$$\Delta Signal = \frac{A_{ObjectShadow}}{A_{Tot\_OWG}} = \frac{A_{ObjectShadow}}{n \cdot A_{OWG}} = \frac{1}{n} \cdot \frac{A_{ObjectShadow}}{A_{OWG}}$$

n=0, 1, 2, . . . (number of receiver-OWG)

This means that a change in signal caused by an object deteriorates as the number of optical waveguides employed increases.

SUMMARY OF THE INVENTION

The object of the invention is to provide a device to detect and/or characterize individual moving objects having very small dimensions which enables the objects moving past the optics to be reliably registered and/or characterized irrespective of the number of optical waveguides used.

This object has been achieved in accordance with the invention by the characteristics outlined in claim 1. Favorable embodiments of the invention are cited in the subordinate claims.

To detect the small objects both the very small mechanical dimensions as well as the optical coupling characteristics of the optical waveguides are exploited. The mechanical dimensions of the optical waveguides are in the order of magnitude of the objects that are to be measured which means that additional beam-forming optical elements to recognize the objects are not required. Moreover, the coupling characteristics of the waveguides when installed, particularly the restricted incoming beam angle typical of optical waveguides, prevent the input of optical interfering signals produced by outside sources of light due to the way the light is guided through total reflection inside the OWG.

According to the invention, the outputs of the emitter-optical waveguides and the inputs of the receiver-optical waveguides are arranged in the form of a ring on a common plane.

In a preferred embodiment of the invention, the optical waveguides are arranged in a ring in such a way that each output of an emitter-optical waveguide is located opposite an input of a receiver-optical waveguide. Here, provision is particularly made for the emitter and the receiver-optical waveguides to be arranged alternatively along the circumference of the ring.

This produces a detection volume that is defined by the area enclosed by the optical waveguides and the diameter of the optical waveguides.

The detection volume takes the form of a disk whose thickness is determined by the diameter of the OWG fibers and which is preferably within the order of magnitude of the objects that are to be measured, the cross-section of this disk in the direction of movement of the objects being significantly smaller than the cross-section transversal to the direction of movement of the objects. Due to the narrow, disk-shaped detection volume, very good detection sensitivity is produced for small objects following each other at a rapid rate.

In order to additionally increase the detection sensitivity, provision can be made according to the invention for the wavelength of the light emitted by the light beam emitter to correspond to at least one absorption wavelength of the object. This is particularly advantageous for the detection of objects that are virtually transparent in daylight, such as drops of liquid. Many liquids have a distinct absorption behavior within the infrared range of light.

The evaluation electronics comprise at least one amplifier connected to the light beam receiver and a microprocessor control.

The microprocessor control makes it possible for the evaluation electronics to be optimally adapted to the operating range of the individual components with the aid of such features as variable amplification factors of the amplifier, the subtraction of offsets, an adjustable switching threshold for the threshold value switch and variable light intensity of the light beam emitter. The electronics can be automatically compensated for environmental influences, component aging, soiling of the photo electric sensor, etc.

The detection device described above makes it possible to reliably recognize and/or characterize objects moving through the photo electric sensor while requiring a very small installation space and being largely insensitive to interference.

An application-related embodiment of the invention will now be explained in more detail on the basis of the figures. Further characteristics, advantages and applications of the invention can be derived from the drawings and their description.

DESCRIPTION OF PREFERRED EMBODIMENTS

One possible application of the invention is its use in counting drops of liquid, particularly drops having a diameter in the sub-mm range. Such small drops can be produced by a microdispenser. The microdispenser shoots out drops having a diameter of less than 100 μm from a jet. For many applications, it is necessary to count every single drop that leaves the microdispenser. Moreover, it is sometimes necessary to characterize the drops as well, that means to measure their approximate size and record their trajectory.

Figure 1:
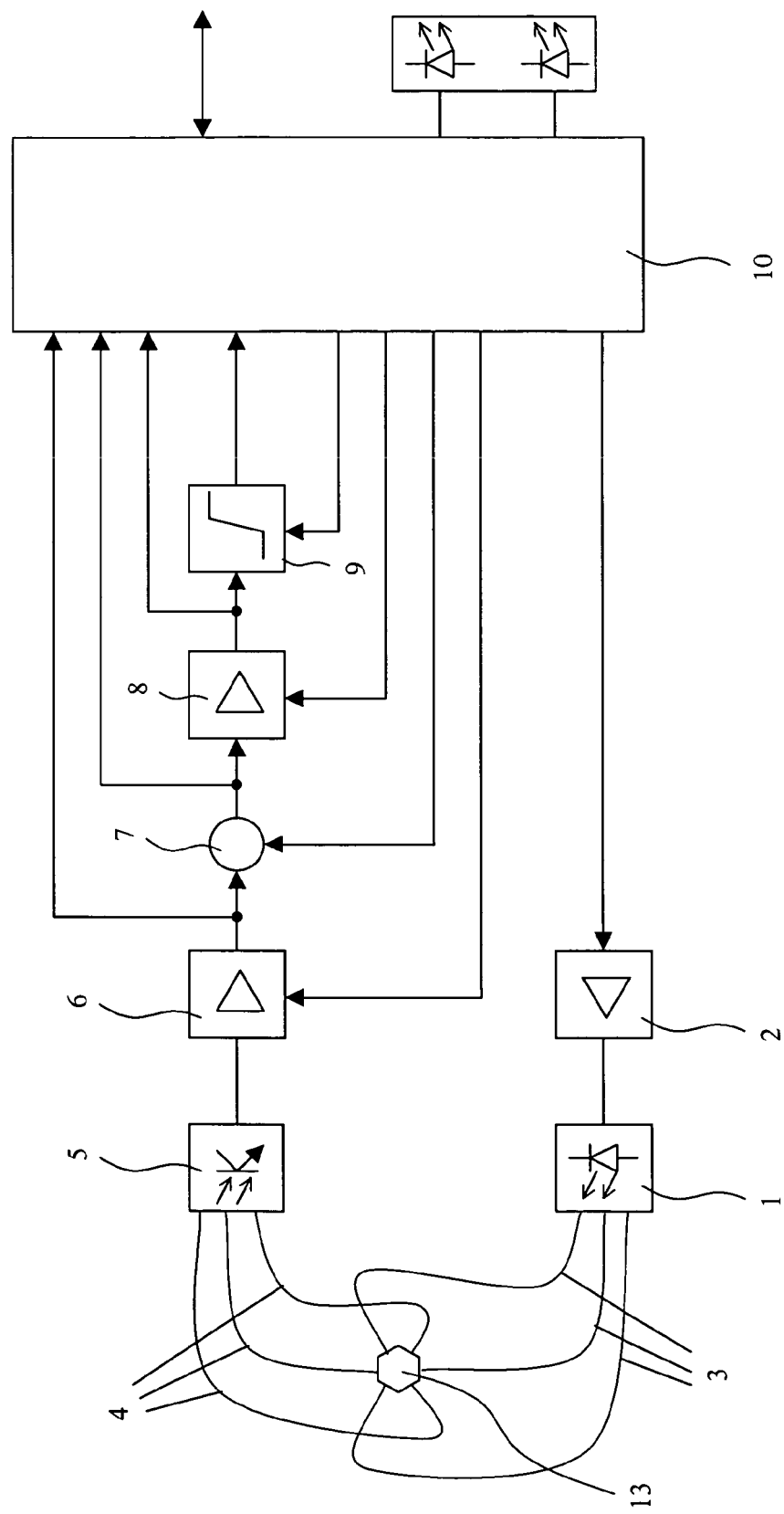
FIG. 1 shows a schematic diagram of a device to detect and/or characterize individual moving objects according to the invention.

As can be seen from FIG. 1, the device comprises a light beam emitter 1, such as a light-emitting diode or a laser diode, that is controlled by a driver 2. The light is fed to a first number of optical waveguides 3 (OWG), three optical waveguides in this embodiment, whose inputs are connected to the light beam emitter 1. The cross-section of the input of the bundle of optical waveguides is adjusted to the cross-section of the light beam emitter used, e.g. circular. The outputs of the individual optical waveguides 3 are arranged in a ring along a circular line. The light beams emitted by the outputs define the optic path of the photo electric sensor.

Each emitter-optical waveguide 3 is associated with a receiver-optical waveguide 4. The inputs of the receiver-OWG are located opposite the outputs of the emitter-OWG 3 and pick up the light beams emitted by the emitter-optical waveguides 3. The optical waveguides 3 and 4 are thus arranged in a ring in emitter/receiver pairs in such a way that the ends of the OWG are located opposite each other and are directed towards the center of the ring. At the same time, the OWG are arranged along the circumference of the ring in such a way that an emitter fiber is located alongside a receiver fiber. The area enclosed by the OWG in conjunction with the diameter of the OWG creates the detection volume 13.

The outputs of the optical waveguides 4 are connected to a light beam receiver 5 which registers the light signals and transforms them into electrical signals. A photo-diode or photo-transistor can, for example, be used as the light beam receiver 5. As mentioned above, an evaluation unit is coupled to the light beam emitter 1 and the light beam receiver 5 and records the change in light intensity of the photo electric sensor produced by the objects passing through the optic path. For this purpose, the electrical signal coming from the light beam receiver 5 is amplified in a first amplifier 6. A voltage is subtracted from this amplified signal in an adder 7 whose absolute value approximately corresponds to the direct voltage portion of the signal voltage. The signal is then amplified again in a second amplifier 8. Changes in the signal at the light beam receiver 5 can now be analyzed over the full range of the amplifier 8 since the direct voltage portion has been removed in the adder 7. A switching threshold is then detected using a threshold value switch 9 and the output signal is fed to a counter circuit which is realized using a microprocessor control 10.

Figure 2:
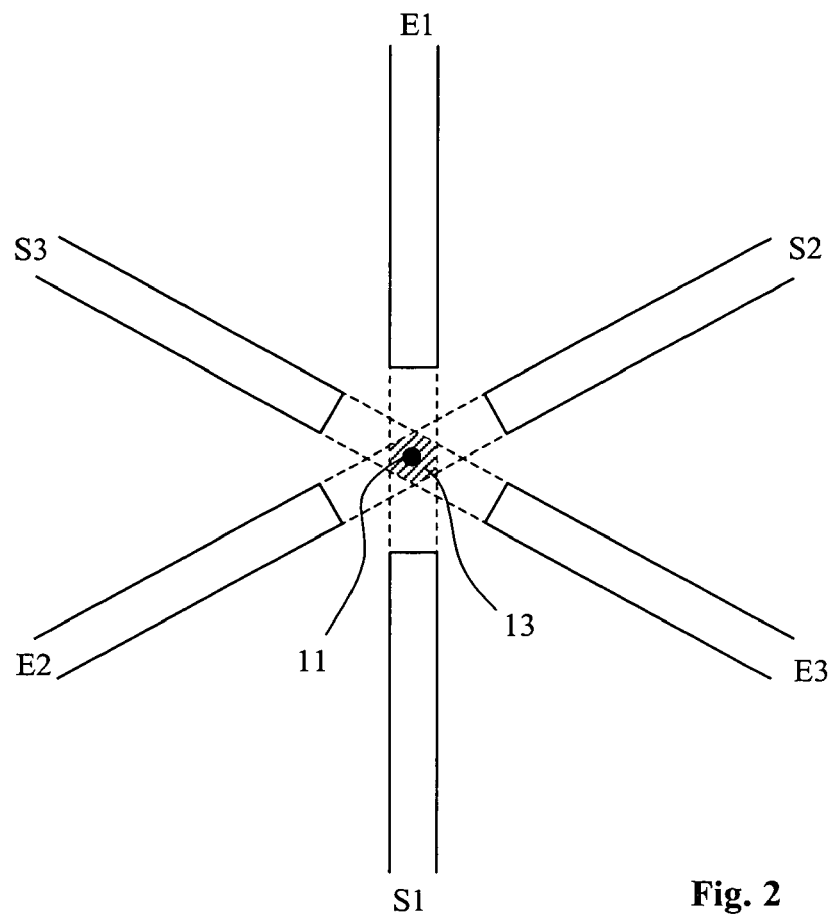
FIG. 2 shows a view from above of a total of six optical waveguides (OWG), three emitter-optical waveguides and three receiver-optical waveguides, arranged in a ring according to the invention.

FIG. 2 shows an enlarged view of the region around the detection volume 13. The optical waveguides 3 form three emitter-OWG S1, S2 and S3. Opposite each of the emitters there is a receiver-OWG E1, E2 and E3 which are formed from the optical waveguides 4. This produces the ring-shaped arrangement of the OWG 3, 4 as described above.

Figure 3:
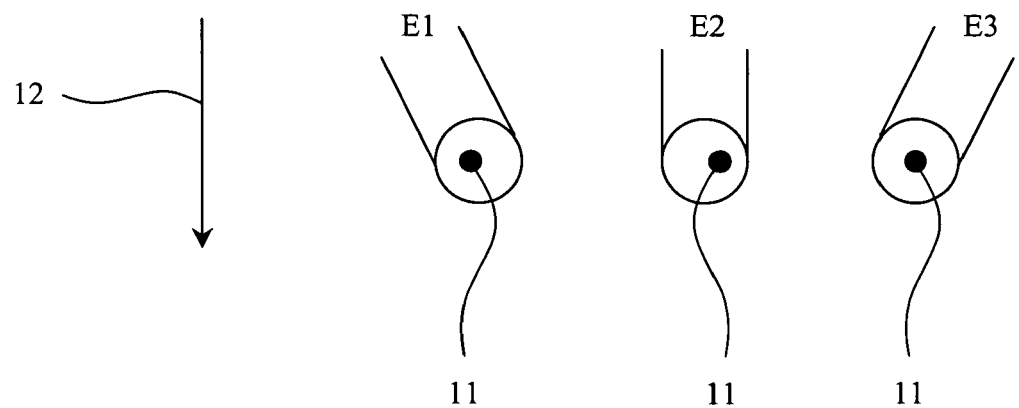
FIG. 3 shows an enlarged view of the receiver-optical waveguide and the shadow cast by an object.

As can be seen in FIG. 3, when an object 11 passes through the detection volume 13, a silhouette of the object 11 is reproduced on each receiver-optical waveguide E1, E2, E3. The object 11 passes through the detection volume in direction 12, i.e. essentially perpendicular to the plane formed by the OWG 3, 4.

Since the silhouette is reproduced on each of the three receiver-OWG at the same time, the change in signal for a passing object is:

$$\Delta Signal = \frac{A_{Tot\_ObjectShadow}}{A_{Tot\_OWG}} = \frac{n \cdot A_{ObjectShadow}}{n \cdot A_{OWG}} = \frac{A_{ObjectShadow}}{A_{OWG}}$$

where

TABLE 3

| | |
|---|---|
| $A_{Tot\_ObjectShadow}$: | Total area of all object shadows |
| $A_{ObjectShadow}$: | Area of one object shadows |
| $A_{Tot\_OWG}$: | Total area of the receiver-OWG |
| $A_{OWG}$: | Cross-sectional area of an OWG |
| n = 0, 1, 2, . . . | Number of receiver-OWG |

It can be seen that the change in signal at the receiver 5 caused by the shading of the receiver-OWG 4 is not dependent on the number n of receiving optical waveguides 4, but only on the ratio of the area of shadow $A_{ObjectShadow}$ of the object 11 to the effective area of an optical waveguide $A_{OWG}$.

Figure 4:
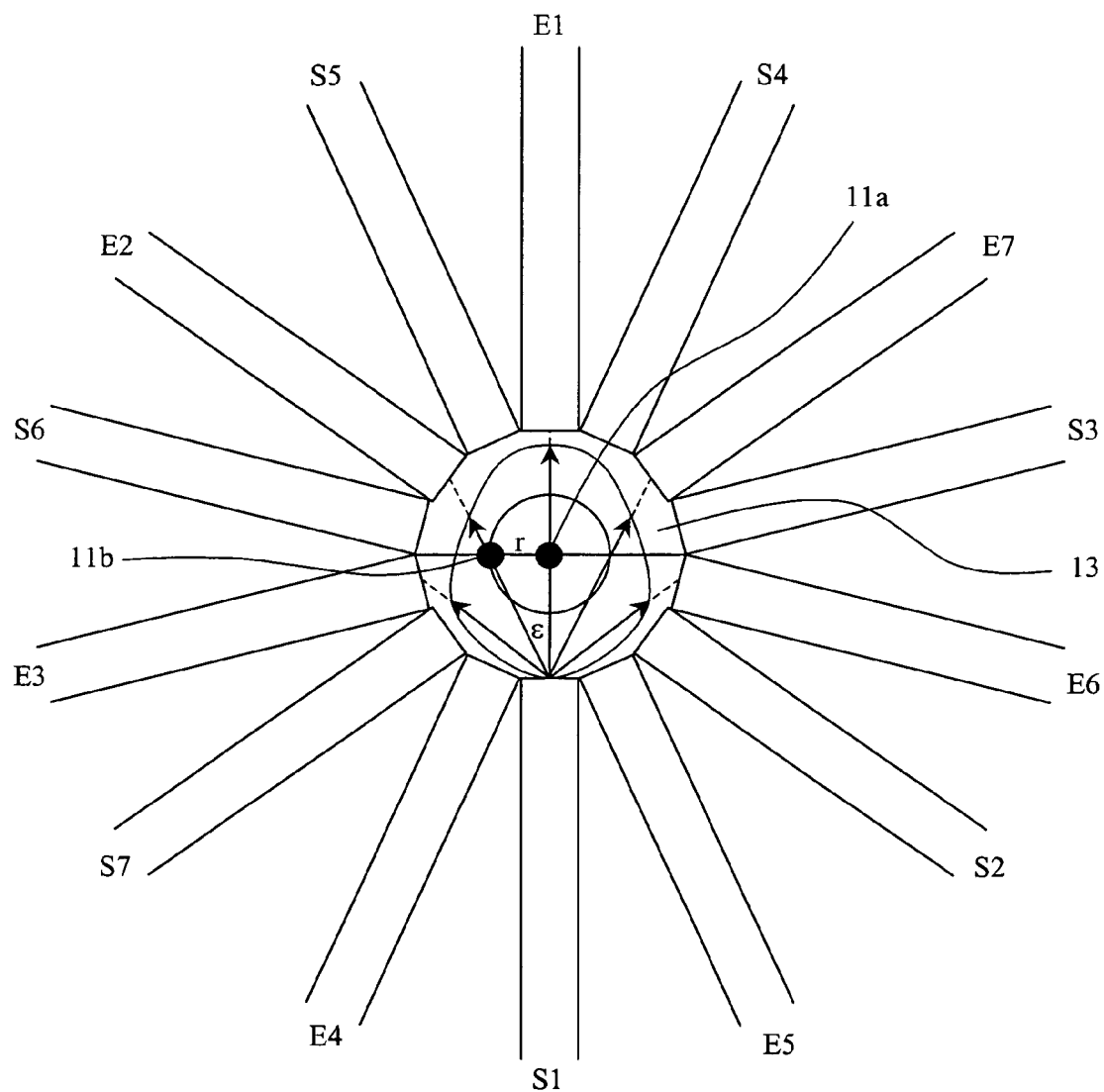
FIG. 4 shows a view from above of a total of fourteen optical waveguides (OWG), seven emitter-optical waveguides and seven receiver-optical waveguides, arranged in a ring according to the invention.

FIG. 4 shows an arrangement according to the invention of fourteen OWG, seven emitter-OWG and seven receiver- OWG. The total number N of emitter and receiver-OWG for the arrangement according to the invention is not arbitrary but is rather ruled by the equation:

$$N=2+4i, \text{ where } i=0, 1, 2, 3, \ldots$$

It is known that the relative radiant power (spatial angle of radiation) at the output of an optical waveguide, here the output of the emitter-OWG S1 for example, is dependent on the angle of reflection s. The spatial angle of radiation can be represented by means of a polar diagram. It can be seen that as the angle of reflection s increases, the relative radiant power decreases. This means that the receiver-OWG E1 associated with the emitter-OWG S1 receives the maximum relative radiant power but that the other receiver-OWG, particularly E2, E7, E3, and E6, also receive a proportion of the radiant power emitted by S1.

Objects passing through the detection volume 13 exactly in the middle thus bring about a different change in signal at the light beam receiver 5 than objects that pass through the detection volume 13 at a different spot. For example, object 11a passes through the detection volume exactly in the middle. This produces maximum shading for each of the associated OWG pairs, e.g. S1-E1, S2-E2, and correspondingly lesser shading for the other receiver-OWG. Another object 11b passes through the detection volume outside the middle at radius r. This object only produces maximum shading for the OWG pairs S3, E3 and S6, E6 and correspondingly lesser shading for the other receiver-OWG. Depending at which radius r the objects pass through the detection region 13, a specific characteristic change in signal is accordingly produced at the light beam receiver 5. The change in signal is consequently a measurement for the radius r at which the objects pass through the detection volume. This statement only holds true under the condition that all recorded objects 11a, 11b have the same consistent size. This makes it possible to roughly determine the position of the objects within the detection volume 13.

If the changes in signal at the individual OWG pairs are analyzed separately, it is even possible to determine the exact penetration position of the object within the detection volume.

IDENTIFICATION REFERENCE LIST

1 Light beam emitter
2 Driver
3 Optical waveguides (emitter S1, S2, S3)
4 Optical waveguides (receiver E1, E2, E3)
5 Light beam receiver
6 Amplifier
7 Adder
8 Amplifier
9 Threshold value switch
10 Microprocessor control 11 object
12 Direction of movement
13 Detection volume

The invention claimed is:

1. A device to detect and/or characterize individual moving objects having very small dimensions which comprises:
   a photo electric sensor having at least one light beam emitter and at least one light beam receiver, wherein objects that are to be measured move through an optical path of the photo electric sensor,
   a plurality of first optical waveguides having first inputs connected to the at least one light beam emitter, the plurality of first optical waveguides having first outputs simultaneously emitting light beams which form the optical path of the photo electric sensor,
   a plurality of second optical waveguides having second inputs simultaneously receiving at least a portion of the light beams emitted by respective optical waveguides of the plurality of first optical waveguides, the plurality of second optical waveguides having second outputs connected to the light beam receiver,
   the first outputs of the plurality of first optical waveguides and the second inputs of the plurality of second optical waveguides being arranged in an alternating manner in the form of a ring on a common plane, each of the first outputs of the plurality of first optical waveguides and the second inputs of the plurality of second optical waveguides directed radially toward the center of the ring, and
   an evaluation unit which is coupled to the light beam receiver and records the change in light intensity of the photo electric sensor produced by the objects passing through the optic path.

2. A device according to claim 1, characterized in that the optical waveguides are arranged in a ring in such a way that each first output of an optical waveguide of said plurality of first optical waveguides is located opposite a second input of an optical waveguide of said plurality of second optical waveguides.

3. A device according to claim 1, characterized in that the area enclosed by the optical waveguides together with the diameter of the optical waveguides define a detection volume.

4. A device according to claim 1, characterized in that the arrangement includes a total number N=2+4i of optical waveguides, where i=1, 2, 3, . . . .

5. A device according to claim 3, characterized in that the cross-section of the detection volume along a first plane is significantly smaller than the cross-section of the detection volume along a second plane transverse to the first plane.

6. A device according to claim 1, characterized in that the wavelength of the light emitted by the light beam emitter corresponds to at least one absorption wavelength of the object.

7. A device according to claim 1, characterized in that the evaluation unit comprises at least one amplifier connected to the light beam receiver and a microprocessor control connected to the amplifier.

8. A device according to claim 2, characterized in that the area enclosed by the optical waveguides together with the diameter of the optical waveguides define a detection volume.

9. A device according to claim 2, characterized in that the arrangement includes a total number N=2+4i of optical waveguides, where i=1, 2, 3, . . . .

10. A device according to claim 3, characterized in that the arrangement includes a total number N=2+4i of optical waveguides, where i=1, 2, 3, . . . .

11. A device according to claim 2, characterized in that the area enclosed by the optical waveguides together with the diameter of the optical waveguides define a detection volume and the cross-section of the detection volume along a first plane is significantly smaller than the cross-section of the detection volume along a second plane transverse to the first plane.

12. A device according to claim 4, characterized in that the area enclosed by the optical waveguides together with the diameter of the optical waveguides define a detection volume and the cross-section of the detection volume along a first plane is significantly smaller than the cross-section of the detection volume along a second plane transverse to the first plane.

13. A device according to claim 2, characterized in that the wavelength of the light emitted by the at least one light beam emitter corresponds to at least one absorption wavelength of the object.

14. A device to detect and/or characterize individual moving objects having very small dimensions which comprises:
- a photo electric sensor having a single light beam emitter and a single light beam receiver, wherein objects that are to be measured move through an optical path of the photo electric sensor,
- a plurality of first optical waveguides having first inputs each connected to the single light beam emitter, the plurality of first optical waveguides having first outputs which emit light to form the optical path of the photo electric sensor,
- a plurality of second optical waveguides having second inputs receiving at least a portion of the light beams emitted by respective optical waveguides of the plurality of first optical waveguides, the plurality of second optical waveguides having second outputs each connected to the single light beam receiver,
- the first outputs of the plurality of first optical waveguides and the second inputs of the plurality of second optical waveguides being arranged in an alternating manner in the form of a ring on a common plane, each of the first outputs of the plurality of first optical waveguides and the second inputs of the plurality of second optical waveguides directed radially toward the center of the ring, and
- an evaluation unit which is coupled to the light beam receiver and records the change in light intensity of the photo electric sensor produced by the objects passing through the optic path.

15. A device according to claim 14, characterized in that the optical waveguides are arranged in a ring in such a way that each output of an optical waveguide is located opposite an input of an optical waveguide.

16. A device according to claim 14, characterized in that the evaluation unit comprises at least one amplifier connected to the light beam receiver and a microprocessor control connected to the amplifier.

* * * * *